(12) United States Patent
Gill et al.

(10) Patent No.: US 11,060,137 B2
(45) Date of Patent: Jul. 13, 2021

(54) METHODS FOR ASSEMBLING DNA MOLECULES

(71) Applicant: CODEX DNA, INC., San Diego, CA (US)

(72) Inventors: John E. Gill, San Marcos, CA (US); Daniel G. Gibson, Carlsbad, CA (US); Lixia Fu, San Diego, CA (US)

(73) Assignee: Codex DNA, Inc., San Diego, CA (US)

( * ) Notice: Subject to any disclaimer, the term of this patent is extended or adjusted under 35 U.S.C. 154(b) by 413 days.

(21) Appl. No.: 15/839,597

(22) Filed: Dec. 12, 2017

(65) Prior Publication Data

US 2018/0163254 A1 Jun. 14, 2018

Related U.S. Application Data

(60) Provisional application No. 62/434,300, filed on Dec. 14, 2016.

(51) Int. Cl.

| | |
|---|---|
| *C12Q 1/68* | (2018.01) |
| *C12N 15/10* | (2006.01) |
| *C12Q 1/686* | (2018.01) |
| *C07H 19/173* | (2006.01) |
| *C12N 9/22* | (2006.01) |
| *C07H 19/073* | (2006.01) |
| *C12P 19/34* | (2006.01) |
| *C12N 15/09* | (2006.01) |

(52) U.S. Cl.
CPC ............ *C12Q 1/686* (2013.01); *C07H 19/073* (2013.01); *C07H 19/173* (2013.01); *C12N 9/22* (2013.01); *C12N 15/09* (2013.01); *C12N 15/10* (2013.01); *C12N 15/1031* (2013.01); *C12P 19/34* (2013.01); *C12Y 302/02027* (2013.01)

(58) Field of Classification Search
CPC .................................................... C12Q 1/686
See application file for complete search history.

(56) References Cited

U.S. PATENT DOCUMENTS

| | | | | |
|---|---|---|---|---|
| 2003/0166169 | A1* | 9/2003 | Padgett | C12Q 1/68 506/30 |
| 2009/0305233 | A1* | 12/2009 | Borovkov | C12Q 1/6811 435/6.16 |
| 2010/0016178 | A1* | 1/2010 | Sussman | C12Q 1/686 506/26 |
| 2010/0035768 | A1* | 2/2010 | Gibson | C12N 9/93 506/17 |
| 2014/0274808 | A1* | 9/2014 | Venter | A61P 31/00 506/26 |

FOREIGN PATENT DOCUMENTS

| | | | | |
|---|---|---|---|---|
| WO | WO 2004/024886 | A2 | 3/2005 | |
| WO | WO 2006/044956 | A1 | 4/2006 | |
| WO | WO-2008054543 | A2 * | 5/2008 | ............ C12N 15/66 |
| WO | WO-2010025310 | A2 * | 3/2010 | ............ C12N 15/66 |
| WO | WO 2012/051327 | A2 | 4/2012 | |
| WO | WO-2012154201 | A1 * | 11/2012 | .......... C12Q 1/6834 |
| WO | WO 2017/059399 | A1 | 4/2017 | |

OTHER PUBLICATIONS

Borovkov et al. High-quality gene assembly directly from unpurified mixtures of microarray-synthesized oligonucleotides. Nucleic Acids Res. Oct. 2010; 38(19):e180 pp. 1-10. Epub Aug. 6, 2010. (Year: 2010).*

Tian J, Ma K, Saaem I. Advancing high-throughput gene synthesis technology. Mol Biosyst. Jul. 2009; 5(7):714-22. Epub Apr. 6, 2009. (Year: 2009).*

Bitinaite et al.: "*User friendly DNA engineering and cloning method by uracil excision*"; Nucleic Acids Research, Mar. 3, 2007, vol. 35, No. 6, pp. 1992-2002.

International Search Report dated Mar. 19, 2018, regarding PCT/US2017/065877.

Klein et al.: "*Multiplex pairwise assembly of array-derived DNA oligonucleotides*"; Nucleic Acids Research, Nov. 8, vol. 44, No. 5, e43, pp. 1-10.

Kodumal et al.: "*Total synthesis of long DNA sequences: synthesis of a contiguous 32-kb polyketide synthase gene cluster*"; Proceedings of the National Academy of Sciences USA, Oct. 20, 2004, vol. 101, No. 44, pp. 15573-15578.

\* cited by examiner

*Primary Examiner* — Teresa E Strzelecka
*Assistant Examiner* — Olayinka A Oyeyemi
(74) *Attorney, Agent, or Firm* — DLA Piper LLP (US)

(57) ABSTRACT

The invention provides compositions and methods for assembling a DNA molecule having a desired sequence. The methods involve contacting a DNA polymerase, dNTPs, and a plurality of pairs of oligonucleotides. The oligonucleotides of a pair have a portion of the desired sequence, and an internal sequence that overlaps and is complementary to an internal sequence of the other oligonucleotide of the pair, and, when arranged in order, they have at least a portion of the desired sequence. The oligonucleotides also have a 3' or a 5' primer binding sequence having a binding site for a primer. The oligonucleotides that correspond to the end oligonucleotides of the desired sequence also have a universal 3' flanking sequence and a universal 5' flanking sequence, respectively. The methods involve performing a first amplification reaction on the plurality of pairs of oligonucleotides; removing the 3' and 5' primer binding sequences from the plurality of pairs of oligonucleotides; and subjecting the plurality of pairs of oligonucleotides to an assembly reaction to thereby assemble the dsDNA molecule having the desired sequence.

26 Claims, 6 Drawing Sheets

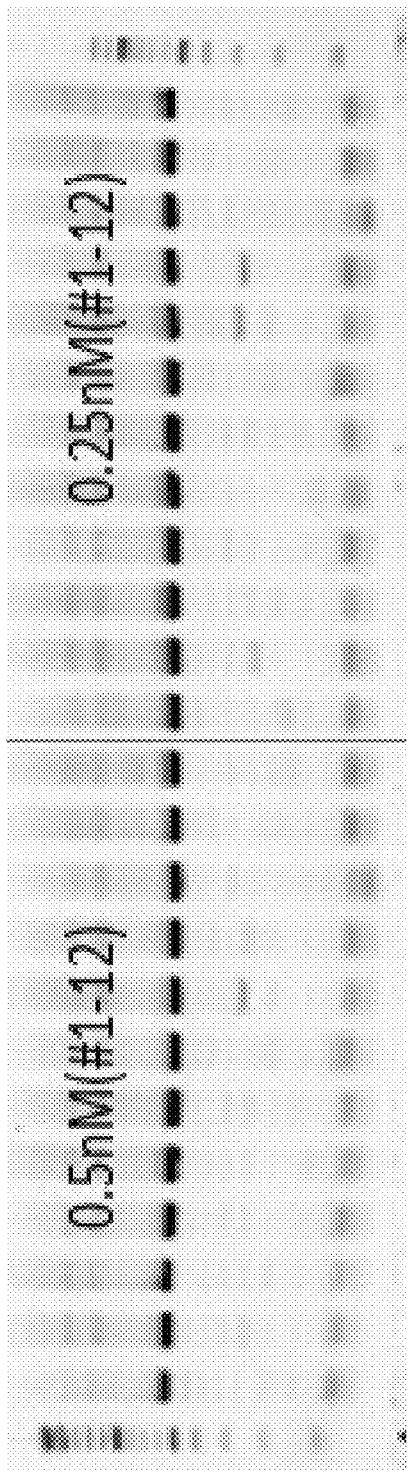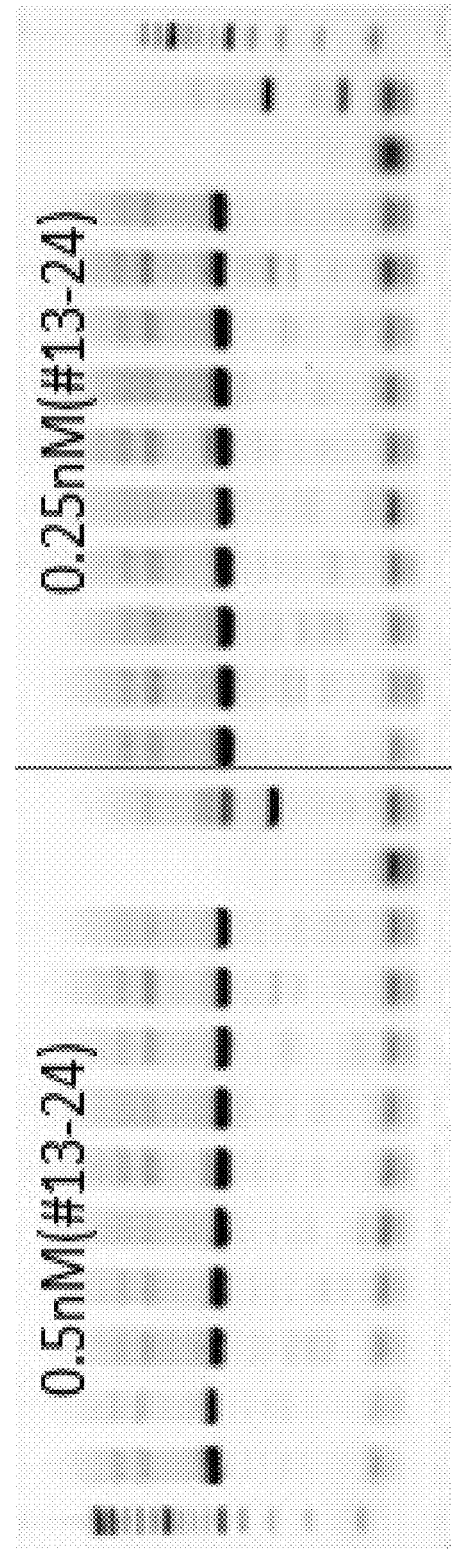
FIGURE 2A
FIGURE 2B

METHODS FOR ASSEMBLING DNA MOLECULES

CROSS-REFERENCE TO RELATED APPLICATIONS

This application claims benefit of priority under 35 U.S.C. § 119(e) of U.S. Ser. No. 62/434,300, filed Dec. 14, 2016, the entire contents of which is incorporated herein by reference in its entirety.

FIELD OF THE INVENTION

The invention pertains to processes and compositions for the assembly of nucleic acid molecules.

BACKGROUND OF THE INVENTION

The synthesis and assembly of DNA molecules remain critical technologies in the field of molecular biology. In particular, the ability to readily assemble multiple double-stranded DNA molecules in a correct order to yield a functional gene or nucleic acid construct (e.g. a vector) is presently an important objective in molecular biology. Existing techniques often involve the parallel synthesis of oligo-nucleotide fragments with a subsequent assembly of the fragments into a larger DNA molecule. Many techniques also require the identification and use of restriction sites for cleavage by a particular restriction enzyme to serve as sites for restriction enzyme cleavage and integration of a sequence of interest. This may be followed by cloning in a suitable host to yield the final nucleic acid construct. While these techniques are often useful, the user encounters difficulty with the assembly of a construct containing multiple genes of interest. A number of additional techniques have been developed to circumvent these difficulties. These solutions often involve some method of disrupting restriction sites. These techniques are also often labor intensive, such as splicing by overlap extension or other methods of generating single-stranded overhangs.

Other conventional methods of oligonucleotide assembly rely on partitioned or array-based oligos in which they are pooled and assembled together without regard to how the oligos may interact with each other in the reaction as a whole. Often, array-based oligos are amplified as single oligos and then flanks are removed using restriction enzymes, which can leave partially inhibiting "scar" sequences on the DNA. These scar sequences can make it difficult to assemble the oligos into higher order DNA assemblies.

It would therefore be useful to have methods of assembling DNA molecules that are easy to use, not labor intensive, and that do not leave "scar" sequences on the DNA.

SUMMARY OF THE INVENTION

The invention provides methods for the assembly of DNA molecules having a desired sequence. In one embodiment a plurality of pairs of overlapping oligonucleotides are amplified (e.g., via PCR) in a method that leverages conserved primer binding sequences at the termini of each oligonucleotide in the pair. The conserved flanking sequences prohibit the oligonucleotide pairs from assembling with one another to form the DNA molecule of desired sequence at an initial stage, and can also serve as 3' and/or 5' primer binding sequences. After forming couplets and amplifying the oligonucleotide pairs, the conserved flanking (primer binding) sequences that inhibit assembly are removed, for example by using a process of scarless flank removal (SFR). The oligonucleotides can then be assembled (e.g., a PCR reaction or a variant thereof) into the DNA molecule of desired sequence. The pairs of oligonucleotides that comprise the end oligonucleotides of the DNA molecule of desired sequence can also comprise additional, universal 3' and 5' flanking sequences, which can be utilized for amplification of the DNA molecule of desired sequence after assembly. The methods are useful for producing DNA molecules de novo and with very low occurrences of nucleotide errors. Constructs produced by the methods can also be subsequently assembled into larger DNA molecules, by the same method or using other methods. In various embodiments nucleic acid molecules assembled by the methods can be further assembled into larger nucleic acid molecules by GIBSON ASSEMBLY®, or other DNA assembly techniques.

In a first aspect the invention provides methods for assembling a DNA molecule having a desired sequence. The methods involve a step of a) contacting a DNA polymerase, dNTPs, and a plurality of pairs of oligonucleotides, wherein each oligonucleotide of a pair comprises a portion of the desired sequence, and the oligonucleotides of a pair comprise an internal sequence that overlaps and is complementary to an internal sequence of the other oligonucleotide of the pair. When the plurality of pairs of oligonucleotides is schematically or illustratively arranged in order, adjacent to each other and according to their internal sequences they comprise at least a portion of the desired sequence. The oligonucleotides can also have a 3' or a 5' primer binding sequence. The desired sequence has a 3' end and a 5' end, and the oligonucleotide pairs that make up the 3' and 5' ends of the desired sequence can also have a universal 3' flanking sequence and a universal 5' flanking sequence, respectively. The methods can also involve a step of b) performing a first amplification reaction on the plurality of pairs of oligonucleotides, and a step c) of removing the 3' and 5' primer binding sequences from the plurality of pairs of oligonucleotides; and a step d) of subjecting the plurality of pairs of oligonucleotides to an assembly reaction to assemble the dsDNA molecule having the desired sequence. In some embodiments the methods are performed in the order of steps recited herein, e.g., steps a-d. The methods can further involve one or more step(s) of forming a plurality of couplets from the plurality of pairs of oligonucleotides, which can be done prior to the first amplification step.

In some embodiments the first amplification reaction further contains primers that bind to the 3' and 5' primer binding sequences. When the universal 3' flanking sequence and the universal 5' flanking sequence are used, they can be present to the inside of the 3' and 5' flanking sequences, respectively. In some embodiments the methods can involve a step of removing at least a portion of the universal 3' flanking sequence and the universal 5' flanking sequence. The first amplification reaction can be PCR, PCA, a variant procedure of PCR or PCA, or any DNA amplification method and can have a denaturation phase, an annealing phase, and an extension phase. The methods can also involve a second, and optionally additional, amplification reactions.

In some embodiments the 5' and 3' primer binding sequences on an oligonucleotide pair are not complementary to each other. The method can assemble a plurality of DNA molecules of desired sequences, which in some embodiments are a plurality of distinct genes. The pairs of oligonucleotides can be comprised on a solid support, for example a nucleic acid array. In some embodiments at least 15 pairs of oligonucleotides or couplets are present on the array. The oligonucleotides or couplets can comprise from 60 to 100 nucleotides and in some embodiments the primer binding sequences can have from 8 to 30 nucleotides. In some embodiments the dsDNA molecule assembled is a nucleic acid construct, for example a plasmid, an artificial chromosome, or a functional gene.

In some embodiments a first pair of oligonucleotides or couplets has a first set of 3' or 5' primer binding sequences, and a second pair of oligonucleotides or couplets has a second set of 3' or 5' primer binding sequences, i.e. the pairs of oligonucleotides or couplets contain at least two sets of 3' or 5' primer binding sequences, but can contain multiple sets. In some embodiments the 3' and 5' primer binding sequences do not have a restriction site for a restriction enzyme. In some embodiments the 3' and 5' primer binding sequences are removed by the action of one or more enzymes that specifically cleave the primer binding sequences, and the one or more enzymes can lack a restriction enzyme. In some embodiments the one or more enzymes contain uracil DNA glycosylase, endonuclease VIII, or exonuclease T, or a combination of enzymes containing one, or two, or all three of them.

In some embodiments the desired DNA molecule is a pre-determined sequence. In some embodiments the plurality of oligonucleotide pairs can be contained in a single container and form at least two couplets, and the at least two couplets can have distinct sets of 3' or 5' primer binding sequences and the primers can bind specifically to the at least two couplets. Any of the methods disclosed herein can involve a step of forming the plurality of pairs of oligonucleotides into a plurality of couplets. Any of the methods can be performed in a single container, and any of the methods can be an automated method. In various embodiments the oligonucleotides that make up the pairs of oligonucleotides are from about 50 to about 200 nucleotides in length. The methods can assemble a dsDNA molecule, which can be of a size greater than 5 Mbp. In any of the methods the nucleic acid molecule of desired sequence can be a scarless DNA molecule.

In another aspect the invention provides compositions containing a DNA polymerase, dNTPs, and a plurality of oligonucleotides formed into couplets, which can be any plurality of oligonucleotide pairs or couplets described herein. Each couplet can contain an internal sequence that comprises a portion of the desired nucleic acid sequence, and when the plurality of couplets is arranged in schematic order, adjacent to each other and according to their internal sequences they comprise at least a portion of a desired nucleic acid sequence. Each couplet can also have a 3' or a 5' primer binding sequence, and each couplet contains a sequence that overlaps and is complementary to a portion of a sequence from an adjacent couplet. The desired nucleic acid sequence has a 3' end and a 5' end, and in some embodiments the couplets that make up the 3' and 5' ends of the desired sequence can also have a universal 3' flanking sequence and a universal 5' flanking sequence, respectively. The composition can be contained in a single container and can, optionally, also contain an effective amount of a preservative. In various embodiments at least 50% of the oligonucleotides in the mixture can be present in a couplet. In some embodiments the couplets overlap at least 33% of their sequences.

DESCRIPTION OF THE DRAWINGS

FIGS. 2A and 2B present an illustration of the gel produced from the assembly method of the invention in which 500 bp constructs were assembled, as described in Example 1.

DETAILED DESCRIPTION OF THE INVENTION

Figure 1:
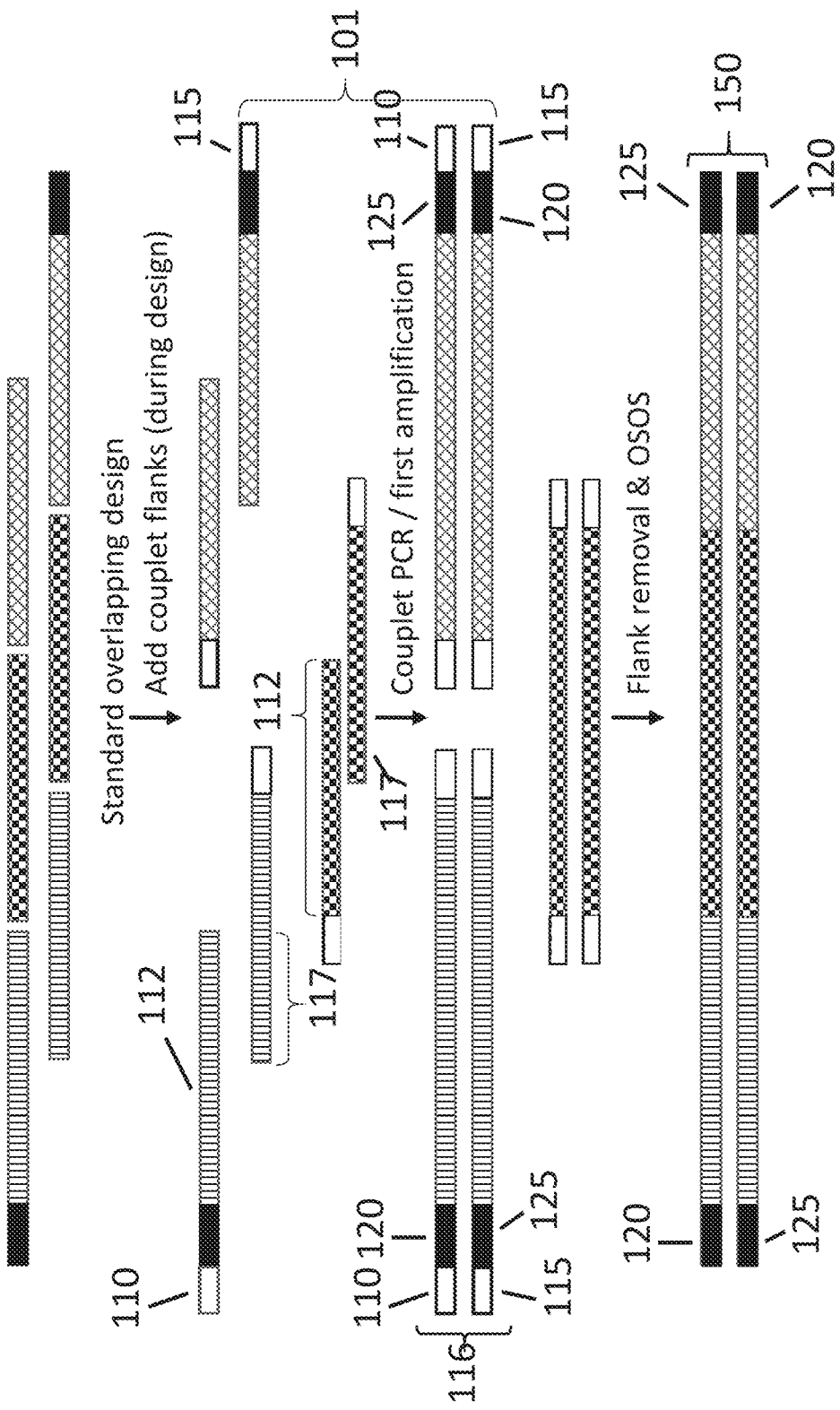
FIG. 1 is a schematic illustration of an amplification and/or assembly reaction of the invention.

The invention provides methods for amplifying and/or assembling a DNA molecule having a desired sequence. The methods involve contacting a DNA polymerase, dNTPs, and a plurality of pairs of oligonucleotides to form a mixture. Each oligonucleotide of a pair has a portion of the desired sequence, and the oligonucleotides of a pair also have an internal sequence that overlaps and is complementary to an internal sequence of the other oligonucleotide of the pair. The oligonucleotide pairs can at least partially bind to form couplets. When the plurality of pairs of oligonucleotides are arranged in order, adjacent to each other and according to their internal sequences they comprise at least a portion of the desired sequence. The oligonucleotides of a pair or couplet also have a 3' or a 5' primer binding sequence for amplifying the pair and discouraging inappropriate annealing. The nucleic acid of desired sequence has a 3' end and a 5' end, and the oligonucleotide pairs or couplets that correspond to the 3' and 5' ends of the nucleic acid of desired sequence can additionally have a universal 3' flanking sequence and a universal 5' flanking sequence, respectively, which is useful in downstream assembly and/or amplification. Any of the methods disclosed herein can involve one or more steps of forming a plurality of couplets from the plurality of pairs of oligonucleotides. In some embodiments the methods involve performing a first amplification reaction on the plurality of pairs of oligonucleotides or couplets in the mixture; removing the 3' and 5' primer binding sequences from the plurality of pairs of oligonucleotides or couplets; optionally subjecting the plurality of pairs of oligonucleotides or couplets to a second amplification reaction using the universal 3' and 5' flanking sequences; and subjecting the plurality of pairs of oligonucleotides or couplets to an assembly reaction to thereby assemble the dsDNA molecule having the desired sequence.

The invention provides a number of advantages over other methods of assembling DNA molecules. By pairing oligonucleotides into "couplets" the overall complexity of the reactions is effectively reduced, allowing for a more robust assembly reaction because the oligo pairs can find their complementary partners with a higher likelihood and with greater specificity than if not coupled. DNA assembly procedures are more effective when longer oligos are used as building blocks, but array-based oligos can accumulate an unacceptable number of errors during the synthesis process. It has therefore been necessary to balance synthesis with oligos that are short enough to keep errors low yet long enough to enable efficient DNA assembly. By pairing the oligos together according to the invention to form couplets their complexity is reduced and they are effectively "lengthened" and the need to produce excessively long oligos at the onset an assembly procedure is eliminated.

During the oligo design and synthesis process (e.g. on an array) conserved flanking sequences, which can be 3' and 5' primer binding sites, are introduced into the oligos on the 3' and/or 5' ends of each oligo. The conserved flanking sequences present at the end of each oligo in a pair can be different and non-complementary. The flanking sequences prevent the oligo pairs from interacting with each other and annealing to each other, due to unfavorable thermodynamic factors. Thus, the overall complexity of the DNA assembly reaction is reduced. The use of distinct 3' and/or 5' primer binding sequences on specific oligo pairs or couplets allows for the selective amplification of specific oligo pairs or couplets in a complex mixture of starting oligonucleotides. When starting oligonucleotide pools are aliquoted to separate containers corresponding primer (or primer pairs) can be placed into each container to selectively amplify the oligonucleotide pair that correspond to the primer or primer pair used. Thus, one can selectively amplify the desired portion of the nucleic acid molecule to be assembled in each separate container. At the downstream assembly step of the method the flanking sequences can be removed, for example by scarless flank removal (SFR) as described herein prior to assembly of the DNA molecule of desired sequence.

Another advantage is that the present invention allows for the amplification of oligonucleotides even when they are present in the reaction in limited supply, for example when present on a solid support (e.g., a microarray). Oligos synthesized on solid phase platforms are typically present at concentrations that render them unsuitable for assembly, but the present invention avoids this disadvantage and allows them to be amplified and easily assembled into larger nucleic acid molecules.

Additional advantages in the methods include the suppression of errors. The pairing of the oligonucleotides into couplets forces the overlapping regions to anneal in a way that selects for oligos with fewer errors, thus giving a statistical preference for amplifying the oligos with fewer or no errors. The present methods are therefore also methods for producing nucleic acids having a reduced error rate compared to conventional methods of amplification and assembly. This is an additional advantage not available with conventional array-based oligos or conventional methods.

Still another advantage of the invention is the ability to achieve "scarless" sequence removal, such as scarless flank removal (SFR). Previously there has been no appropriate method for removing conserved primer binding sequences from PCR products or otherwise undesired sequences in the dNA. Any of the methods disclosed herein can use scarless sequence removal, meaning that all nucleotides related to the flanking primer binding sequences, or to another undesired sequence, are removed and a pre-determined sequence of DNA can be synthesized and assembled in the methods. The invention provides a method for removing DNA from the terminal ends of PCR or other amplification or assembly method products without the use of restriction enzymes. The method therefore permits the use of a larger number of primer binding sequences because it does not rely on the sequence constraints imposed by restriction enzymes. Furthermore, the "scarless" removal of the primer binding sequences on the oligonucleotide pairs or couplets allows for a more robust assembly process to proceed because the DNA overlaps are exposed after this removal is achieved. In the invention methods of DNA assembly can therefore be automated or performed in programmable steps, and can be performed in a stepwise fashion. Nevertheless, in some embodiments restriction sites and restriction enzymes can be located on the 3' and/or 5' primer binding sequences and used to conduct the methods.

Oligonucleotide Pairs

Figure 3:
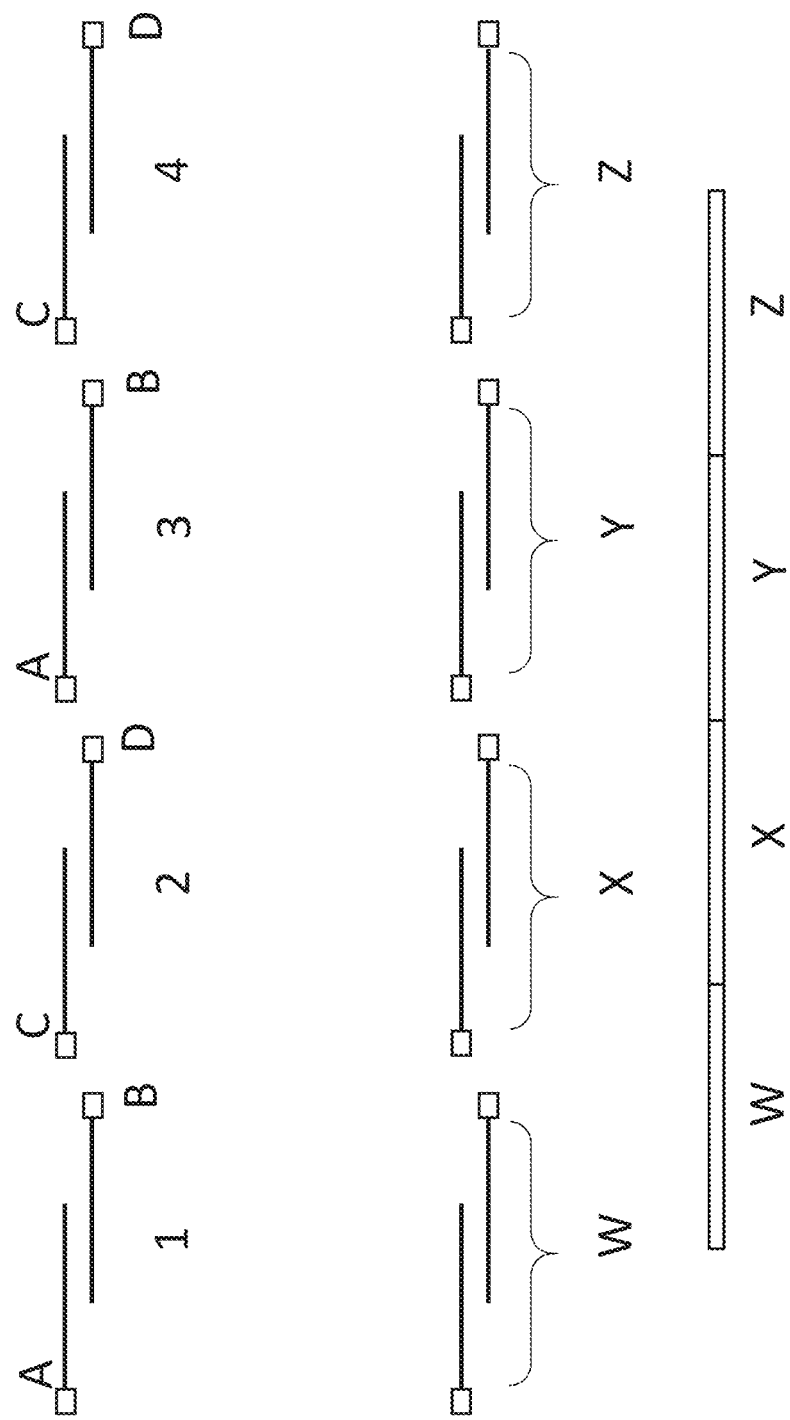
FIG. 3 is a schematic illustration showing the use of alternating sets of 3' and 5' primer binding sequences, which have primer binding sites.
Figure 4:
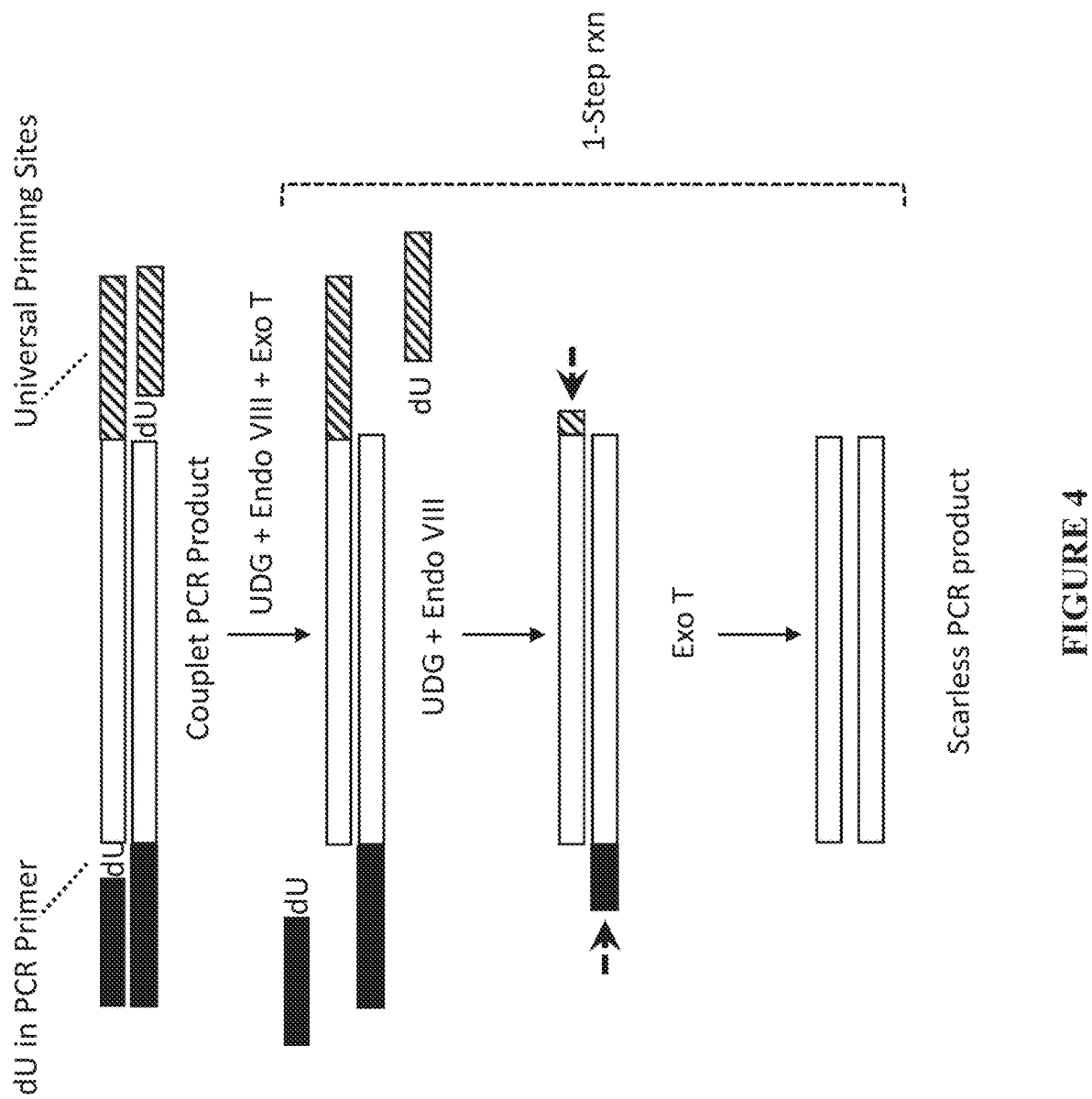
FIG. 4 is a schematic illustration of scarless flank removal.
Figure 5:
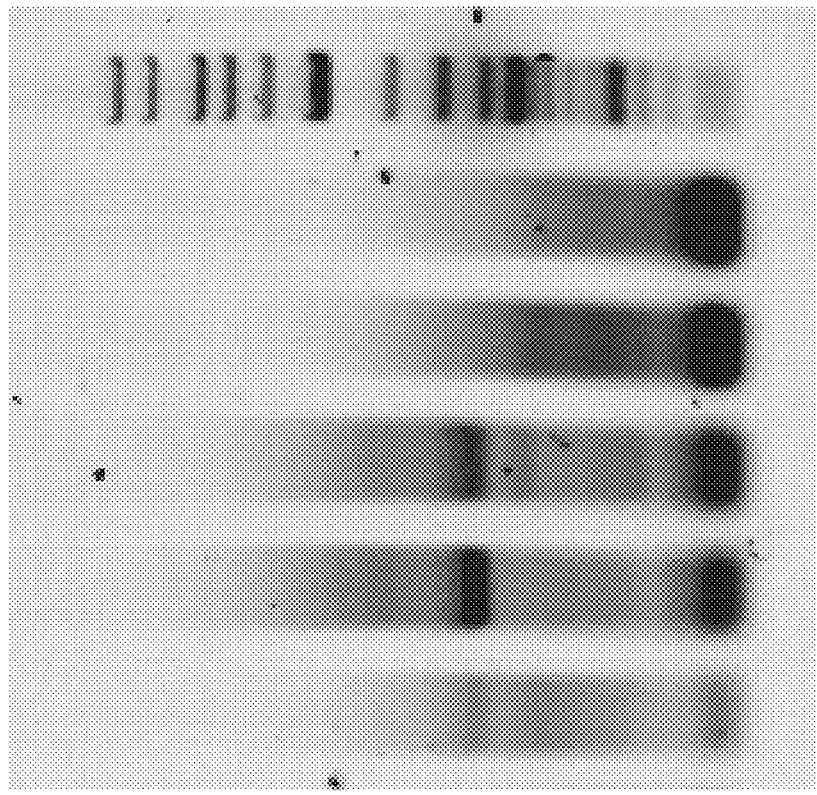
FIG. 5 presents an illustration of the gel produced from various embodiments of the assembly method of the invention for the assembly of a 1.2 kb product, as described in Example 2. The gel presents the results of PCA assembly after scarless flank removal. Lane 1: Pool 3; Lane 2: Pool 1. Lane 3: Pool 2.

The oligonucleotide pairs or couplets used in the methods have certain characteristics. Each oligonucleotide of a pair contains a portion of the desired sequence of the DNA molecule. Each oligonucleotide of a pair has an internal sequence 112, which contains an overlapping and complementary sequence to an internal sequence of the other oligonucleotide of the pair. When the plurality of pairs of oligonucleotides are schematically or illustratively arranged in order (e.g. as depicted in FIGS. 1 and 3), adjacent to each other and overlapping according to their internal sequences they comprise at least a portion of the desired sequence, and can comprise a set of couplets or oligo pairs that comprise the entire desired sequence when each oligo is extended. One or both oligonucleotides in a pair or couplet can overlap with oligonucleotides in one or more adjacent pairs when arranged according to their internal sequences. One or both oligonucleotides in a pair or couplet can overlap with a third oligonucleotide and the three can form a triplet. The oligonucleotides can also have a 3' primer binding sequence 110 and/or a 5' primer binding sequence 115 for amplifying the oligo pairs and discouraging undesirable annealing, and in some embodiments each oligonucleotide of a pair has the 3' and/or 5' primer binding sequence. Furthermore, oligo pairs representing the end oligonucleotides of the DNA molecule of desired sequence can additionally have a universal 3' flanking sequence 120 or a universal 5' flanking sequence 125, which can be present inside of the 3' and 5' primer binding sequence 110, 115, respectively. The end oligonucleotides are those oligos that comprise the ends of the desired sequence that is assembled, and are depicted in FIG. 1 having the flanking sequences 120 and 125. The end oligonucleotides can be contained in an oligonucleotide pair or couplet that overlaps only one other pair or couplet, the adjacent one, in the set of oligonucleotides comprising the desired nucleic acid sequence. In some embodiments the end oligonucleotides are the only oligonucleotides that comprise the universal 3' and/or 5' flanking sequences 120, 125. In one embodiment when the plurality of pairs of oligonucleotides are arranged in order, adjacent to each other and overlapping according to their internal sequences, and considering only their internal sequences and, optionally, the universal flanking sequences, they together comprise the sequence of the DNA molecule of desired sequence on one or the other strand (not counting any 3' and/or 5' primer binding sequences on said pairs of oligonucleotides), as generally depicted in FIG. 1. When the desired nucleic acid molecule is a double-stranded DNA, the plurality of pairs of oligonucleotides can also comprise, at each nucleotide in the DNA molecule, a nucleotide on at least one of the two strands of the double-stranded DNA molecule. The nucleotides of the opposite strand are, of course, filled in by DNA polymerase extension during amplification and/or assembly to form the desired double-stranded DNA molecule. This is also illustrated in FIG. 1 where after a first amplification the plurality of pairs comprise the DNA molecule of desired sequence, which can be assembled to form the DNA molecule of desired sequence as depicted at the bottom of FIG. 1.

In the methods a first (and optionally second and subsequence) amplification reaction(s) can be performed on the plurality of pairs of oligonucleotides until a suitable quantity of pairs of oligos are present. The 3' and 5' primer binding sequences 110, 115 can then be removed from the plurality of pairs of oligonucleotides, and the plurality of pairs can be subjected to an assembly reaction to thereby assemble the dsDNA molecule having the desired sequence. The pairs can be readily assembled and the assembled nucleic acid further amplified because the end oligonucleotides contained the universal 3' and 5' primer binding sequences 120, 125, which are still present at the ends of the assembled molecule.

The desired sequence can be a pre-determined sequence, meaning that the sequence assembled in the method is a specific sequence known or determined by the user prior to conducting the method. The desired sequence to be assembled in the method is therefore predictable. Random homologous recombination does not normally result in a "desired" sequence because the user cannot predict the precise location the recombination will occur, and therefore cannot predict the specific sequence that will result from the method. The double-stranded nucleic acid molecule can be a DNA molecule, an RNA molecule, an rRNA molecule, a cDNA molecule, or any nucleic acid molecule. In various embodiments the nucleic acid molecule can be a gene or a functional gene and can encode a protein or polypeptide, or can be a regulatory sequence, or a "housekeeping" gene sequence, or any nucleic acid sequence. The nucleic acid molecule can also be a portion of a gene, a whole gene, a gene pathway, a whole genome (e.g. of a bacteria, algae, cyanobacteria, virus, etc), a promoter, a terminator, a regulatory sequence, a CRISPR/Cas9 gRNA template, a DNA-based computer memory, or any other nucleic acid sequence. In various embodiments the nucleic acid sequence can be a portion of any of the types of nucleic acid sequences above, e.g., at least 25% or at least 50% or at least 75% or 25-99% or 50-99% or 75-99% of a gene, portion thereof, or of any of the nucleic acid sequences recited above.

Referring to FIG. 1 the pairs of oligonucleotides at least partially bound to each other ("couplets") have particular parts, including an internal sequence 112, which contains a portion of the desired nucleic acid sequence of the DNA molecule to be assembled. The oligonucleotide pairs have at least one portion of the internal sequence 112 that overlaps and is complementary to 117 a portion of the internal sequence of the other member of the pair, and the two oligonucleotides can thereby at least partially bind to each other and form a "couplet." Thus, a pair of oligonucleotides can bind to form a couplet. In various embodiments the couplets are bound to each other by at least one or at least three or at least five or at least eight or at least 10 nucleotides by hydrogen bond pairing. The overlapping portions can at least partially bind to each other by forming hydrogen bonds and thus anneal to each other at the complementary sequence. Examples of oligonucleotide couplets are depicted in FIG. 1. The internal sequences form at least a portion of the desired nucleic acid molecule. In FIG. 1 the desired nucleic acid molecule is depicted as 150, which in this embodiment contains the universal 3' and 5' flanking sequences 120, 125. When the oligonucleotides are assembled in order, adjacent to each other and according to their internal sequences, the oligonucleotides comprise at least a portion of the sequence of the desired dsDNA molecule 150. In some embodiments a portion of the sequence of the desired DNA molecule is contained on each oligonucleotide in the set. In some embodiments all of the oligonucleotides together comprise the nucleic acid sequence of the nucleic acid molecule being assembled, or a complement thereof, as depicted in FIG. 1. The pairs of oligonucleotides can also have a 5' and/or 3' primer binding sequences 115, 110 (or complementary sequence thereof). Complementary or complement sequences refers to standard Watson-Crick base pairing. In some embodiments the 3' primer binding sequence and 5' primer binding sequence on an oligo pair can be different sequences to avoid circularization and self-annealing of the two ends of the couplet or pair. Each oligonucleotide in the pair can thus comprise a primer binding sequence at its 3' and/or 5' end. In some embodiments a plurality of oligonucleotide pairs can be present in a single container and form a plurality of couplets, and the plurality of couplets can each have a distinct set of 3' or 5' primer binding sequences, as explained herein. In some embodiments the couplets can be amplified and/or assembled in the single container. The method can therefor also involve the use of at least two sets of primers that bind specifically to the at least two couplets, respectively.

Some pairs of oligonucleotides comprise the ends of the desired dsDNA molecule and are "end oligonucleotides." In addition to the other characteristics of an oligonucleotide or couplet, such as a 3' and/or 5' primer binding sequence, the end oligonucleotides can further comprise a 5' and/or 3' universal flanking sequence 125, 120. The universal flanking sequences 125, 120 can be a primer binding site, and can be a primer binding site of a different sequence or that binds a different primer than the 3' and/or 5' primer binding sequences 110, 115. The universal flanking sequences on the 5' and 3' end oligonucleotides can be the same sequence or a different sequence from each other. The universal flanking sequences allow for downstream amplification and/or assembly of the dsDNA molecule of desired sequence after it has been assembled.

The oligonucleotide pairs utilized in the invention can be synthesized through any convenient method. While various methods of synthesizing oligonucleotides by design are known in the art, one example is in situ synthesis on solid phase microarrays where the solid phase is loaded with a multiplicity of different sequences during the synthesis. But any method of synthesizing oligonucleotides can be used. Oligonucleotides can also be traditional partitioned oligos derived from DNA from a natural source. The oligonucleotides can be formed into couplets after synthesis or other method of obtaining the oligonucleotides. Any of the flanking sequences can be synthesized with the synthesis of the oligonucleotide.

The starting oligonucleotides or couplets can be those present prior to the first amplification step and those on which the first amplification step is performed. The starting oligonucleotides can be annealed together to form couplets. In various embodiments the starting oligonucleotides can be from 10-20 nucleotides or 15-20 or 20-60 nucleotides or 20-80 or 20-100 or 20-200 or 20-225 or 20-250 or 40-60 nucleotides or 40-85 or 40-100 or 40-225 or 50-150 or 50-200 or 50-250 or 60-200 or 60-150 or 60-120 or 60-100 or 60-85 or 80-120 or 40-150 or 40-200 or 40-225 or 40-250 nucleotides, or greater than 40 nucleotides or greater than 50 or greater than 60 or greater than 75 or greater than 100 or greater than 250 nucleotides. The overlapping region in an oligonucleotide pair can be at least 5 bp or at least 8 or at least 10 or at least 12 or at least 15 or at least 17 or at least 20 bp or at least 40 or at least 60 or at least 80 or at least 100 bp or from 5-10 or 5-12 or 5-15 or 5-17 or 5-20 or from about 15 to about 30, or from about 12 to about 35, or from about 15 to about 60 bp, or from about 15 bp to about 120 bp, or from about 20 to about 200 bp, or from about 20 to about 120 bp, or from about 20 to about 100 bp, or from about 20 to about 80 bp, or from about 20 to about 50 bp, or from about 25 to about 40 bp, or from about 20 to about 40 bp in length, or from about 100 bp to about 500 bp, or from about 200 bp to about 700 bp, or from about 200 bp to about 1000 bp, or from about 200 bp to about 1500 bp, or from about 30 to about 200 bases, or from about 20 to about 150 bases, or from about 20 to about 120 bases, or from about 20 to about 100 bases, or from about 20 to about 80 bases, but any suitable length of overlap can be used. Oligonucleotides or oligo pairs can be applied in the method at any suitable concentration, and non-limiting examples include less than 2 nM or less than 3 nM or less than 5 nM or less than 2.5 nM or less than 1.25 nM or less than 1.0 nM or less than 700 fmol or less than 500 fmol or less than 250 fmol or less than 100 fmol or less than 1 fmol, or 0.5-2 nM or 0.5-5 nM or 2-5 nM or 2-10 nM or 2-20 nM or 1-100 fmol or 1-1000 fmol or 500-1000 attamol or 700-1000 attamol.

Oligonucleotides in an oligo pair can be designed to have an internal sequence that will be part of either strand (e.g. the sense or anti-sense strand) of the nucleic acid molecule of the desired sequence to be assembled. In various embodiments each oligonucleotide in a set of oligonucleotides will have an internal sequence that is part of one of the strands (e.g. the sense or anti-sense strand) of the desired sequence.

In one embodiment the oligonucleotide pairs are part of a set of oligonucleotides, and the set of oligonucleotides, when assembled according to a method of the invention, comprises the nucleic acid molecule having a desired sequence. The set can optionally have primer binding sequences at their 3' and/or 5' ends, and universal flanking sequences on the end oligonucleotides. The set can also include sequences that are subsequently deleted to form the nucleic acid of desired sequence.

Internal Sequence

The oligonucleotides of the invention contain an internal sequence 112. In one embodiment when the oligonucleotide pairs are arranged adjacent to each other and in proper order according to their internal sequences, the internal sequences comprise all or a portion of the sequence of the nucleic acid molecule of desired sequence that is assembled in the methods. The internal sequences of two oligos of a pair at least partially overlap and the oligos of the pair can anneal to each other. A "couplet" is comprised of two oligos that at least partially overlap in their internal sequences and examples are depicted in FIG. 1. The internal sequences can also overlap at least partially with one or more oligonucleotides of an adjacent couplet to form the all or a portion of the sequence of the nucleic acid molecule of desired sequence. Thus, a particular oligo can overlap in some instances with one adjacent oligo to form a pair and in other instances with a second adjacent oligo to form a second, distinct pair. Nevertheless, the oligo pairs or couplets are a set that can be assembled into the nucleic acid of desired sequence. The end oligonucleotides can overlap with an oligonucleotide of only one adjacent oligonucleotide. To be arranged according to their internal sequences means the oligos are arranged adjacent to each other so that the internal sequences together form all or a portion of the sequence of the desired nucleic acid molecule. The internal sequences can also comprise all or a portion of the sequence of the nucleic acid molecule of desired sequence not counting universal flanking sequences on the nucleic acid molecule of desired sequence. In some embodiments the internal sequences can also comprise the overlapping portions of the oligonucleotide pairs. Each such portion of an oligonucleotide can be complementary to a portion of the other oligonucleotide of the pair.

3' and/or 5' Primer Binding Sequences

The oligonucleotides of the invention, and therefore an oligo pair or couplet, can also comprise a 3' and/or a 5' primer binding sequence. The primer binding sequence can be a primer binding site for one or more primers, and is useful during the amplification reactions. In some embodiments each oligo of a pair or couplet comprises a 3' primer binding sequence, or a 5' primer binding sequence. But of course when the oligo pairs are extended to form a full double-stranded nucleic acid molecule a primer binding sequence will be present on both the 3' and 5' ends. FIG. 1 illustrates an example where the oligos in a pair each comprise a 3' primer binding sequence 110 and are extended to a double-stranded nucleic acid with a primer binding sequence on both the 3' and 5' ends 110, 115. In one embodiment the 3' and/or 5' flanking primer binding sequences can be designed and synthesized as part of the oligonucleotides at the stage of oligonucleotide synthesis. The oligonucleotides can be synthesized so that each oligo has either a 3' or a 5' flanking primer binding sequence. When the oligonucleotides anneal to form couplets the couplet can have a primer binding sequence at the 3' and/or 5' end. In other embodiments the 3' and/or 5' primer binding sequences can be added later to the oligonucleotides. The 3' and/or 5' primer binding sequences can also be introduced to the oligonucleotides or oligo pairs subsequent to synthesis. The 3' and 5' primer binding sequences can be introduced by any suitable method, with ligation and amplification being two examples. The primer binding sequences can be introduced as single or double-stranded nucleic acid sequences and can be a known or unknown sequence, as long as it can perform the function of the primer binding sequence. But some oligonucleotides can lack a 3' and/or 5' primer binding sequence. In some embodiments these oligonucleotides that lack a primer binding sequence can be members of a triplet and overlap with two other oligonucleotides, which can each have a 3' and/or 5' primer binding sequence.

Considering an embodiment where oligonucleotide pairs are arranged adjacent to each other and according to their internal sequences to comprise at least a portion of the nucleic acid of desired sequence (e.g. FIG. 1), each oligonucleotide pair has a 3' and/or 5' primer binding sequence on its corresponding distal end. These sequences comprised on a particular pair or couplet can be referred to as a "set" of 3' and/or 5' primer binding sequences. Nevertheless, when the couplet is amplified and extended the double-stranded DNA fragment formed will have a primer binding sequence on both the 3' and the 5' distal ends. Sets of primer binding sequences can be conveniently depicted as letters, numbers, or any symbol that distinguishes one set from a set of different sequence. In some embodiments the oligonucleotides of a pair or couplet contain a set of primer binding sequences that is different from and non-complementary to the set on the adjacent oligonucleotide pair or couplet and thus, they do not anneal to an adjacent oligo pair or couplet. An oligo pair or couplet can also contain different and non-complementary primer binding sequences on their 5' and/or 3' ends, and therefore is prevented from forming a circular DNA molecule by self-annealing. Thus, the primer binding sequences in a set can be different from each other but, in other embodiments, can also be the same. In a particular embodiment two sets of 3' and 5' primer binding sequences are used in a method where the oligonucleotide pairs or couplets are arranged adjacent to each other and according to their internal sequences to form the desired nucleic acid. In this embodiment one set is used on the odd numbered oligonucleotide pairs or couplets (e.g. couplet 1, 3, 5, etc.) and a second, different set is used on the even numbered oligonucleotide pairs or couplets (e.g. couplet 2, 4, 6, etc.). The "even" and "odd" numbered pairs are determined by considering the first oligonucleotide pair or couplet in the above arrangement as the first "odd" number and the second oligonucleotide pair or couplet in the arrangement as the first "even" number, and so on, for example as numbered in FIG. 3A. Utilizing such an arrangement can allow multiple nucleic acid molecules to be assembled from a single pool of couplets and, optionally, in a single reaction in the method because, for example, couplets 1 and 3, or couplets 2 and 4 will not anneal to each other due to the differences in their sequences, even if they have the same set of primer binding sequences. And couplets 1 and 2, or 3 and 4, will not anneal to each other because the primer binding sequences are distinct and non-complementary. Thus, the odd numbered or the even numbered oligo pairs or couplets (i.e. alternate oligo pairs or couplets) can be amplified in a single pool.

Thus, primer binding sequences A and B can represent two primer binding sequences that are different sequences and not complementary and, therefore, do not anneal to each other. A and B together can form a set A-B. Referring to FIG. 3, in one embodiment constructs 1-4 comprise at least one strand of a double-stranded DNA molecule of a desired sequence. An A-B set of flanking primer binding sequences can be placed on the odd numbered oligonucleotide pairs or couplets and a C-D set of flanking primer binding sequences can be placed on the even numbered oligonucleotide pairs or couplets. This arrangement prevents circularization of a couplet by self-annealing and also prevents adjacent couplets from annealing before the intended step in the method. Instead the couplet is preserved and available for amplification until assembly of the DNA molecule is desired. Nevertheless, specific primer binding sequences can be varied and selected based on the needs of the particular application. Thus, in some embodiments each oligo pair or couplet can have the same 3' and/or 5' primer binding sequence if desired (e.g., set A-A). This embodiment might be selected in cases where, for example, the members of the oligonucleotide pair or couplet are short enough that formation of a circular molecule will not occur. In one embodiment the 3' and 5' primer binding sequences do not comprise a restriction site that is cleavable by a restriction enzyme (e.g., a restriction endonuclease).

The actual primer binding sequence can be any appropriate sequence to which a primer can bind. In some embodiments the 3' and/or 5' primer binding sequence is a poly-A sequence. In some embodiments the sequence can be a universal primer sequence. In various other embodiments the sequence can contain one or more uridine nucleotide residues or other nucleotides, that provide a cleavage site for an enzyme to remove the primer binding sequence. Examples include, but are not limited to, having a deoxyuridine every fourth base or every third base or fifth base or every sixth base to make the site a substrate for the enzyme UDG and prepare the sequence for removal by other enzymes. In other embodiments the sequence can have at least one uridine per 5 bases or at least two or at least three uridines per 5 bases. In other embodiments the primer binding sequence can contain a poly-U having four or five or six or seven or eight or nine or ten or more than ten dU nucleotides, or any combination of the above. But in other embodiments the flanking sequence can be a binding site for a restriction enzyme. In other embodiments the site can be designed so it is not a restriction site that will be cleaved by any restriction enzyme. The 3' and/or 5' primer binding sequences can include non-standard bases to which an enzyme is available that cleaves or specifically marks a nucleotide or nucleotide sequence for cleavage and removal by another enzyme. In some embodiments the primer binding sequence(s) can be a site for cleavage by a particular restriction enzyme or group of enzymes. Furthermore, the primer binding sequences can be sites for binding for Cas9 enzyme, and thus CRISPR/Cas9 can be used to cleave off the flanking sequence.

The primer binding sequences of the invention can be any length suitable for a primer binding sequence under the reaction conditions. In various embodiments the primer binding sequence can be from about 6-30 or 8-30 nucleotides in length, or from about 6-40, or 6-25 or 6-20 or 6-15 nucleotides, or 8-25 or 8-20 nucleotides, or from about 10 to about 30 nucleotides or 10-25 or 10-20 nucleotides, or from about 12 to about 25 nucleotides or 12-30 or 12-20 nucleotides, or from about 15 to about 25 nucleotides or from about 15 to about 35 nucleotides or from 15 to about 50 nucleotides or from 10-100 or from 20-250 or from 25 to 350 or from 25 to 500 or from 10 to 1000 nucleotides.

In another embodiment a distinct 3' and 5' primer binding sequence set can be used for each oligonucleotide pair or couplet to be assembled into the DNA molecule of desired nucleotide sequence. This embodiment allows a particular oligonucleotide pair or couplet (i.e. that pair or couplet having the corresponding primer binding sequence) to be assembled in a mixture containing several or all of the oligonucleotide pairs or couplets. In one embodiment various aliquots of synthesized oligonucleotides can be set out separately and a primer or primer set corresponding to a particular primer binding sequence can be used to amplify only certain oligo pairs or couplets (or DNA fragments) in a specific sample mixture.

Universal Flanking Sequences

One or more of the oligonucleotide pairs or couplets that comprise a DNA molecule of desired sequence can have a 3' and/or 5' universal flanking sequence 120, 125. The universal flanking sequence is a sequence that can serve as a primer binding site for the amplification of the assembled dsDNA molecule of desired sequence 150. Primers that bind to these sequences can be provided in an amplification reaction after assembly of the nucleic acid molecule of desired sequence. In some embodiments the end oligonucleotides have a 3' or 5' universal flanking sequence, but not both with respect to the nucleic acid molecule of desired sequence. In some embodiments all of the oligonucleotides being assembled have either a 3' or 5' primer binding sequence, but not both.

In one embodiment the universal flanking sequence is present on only the end oligonucleotides or couplets, i.e., the oligonucleotides corresponding to (and that will form) the sequence of the 3' and/or the 5' ends of the DNA molecule of desired sequence when the pairs or couplets are arranged adjacent to each other and in proper order according to their internal sequences so that the internal sequences comprise the sequence of the nucleic acid molecule of desired sequence assembled in the methods. In some embodiments the universal 3' and/or 5' flanking sequence is present on the end oligonucleotides "inside" the 3' and/or 5' primer binding sequence, i.e. proximal to the 3' and/or 5' primer binding sequence and distal to the internal sequence (e.g. as depicted in FIG. 1). Proximal indicates away from the outer ends of the nucleic acid molecule of desired sequence to be assembled and towards the center or overlapping region in the couplets; distal indicates towards the outer ends. The 3' and/or 5' universal flanking sequences are therefore useful for amplifying the DNA molecule of desired sequence that is assembled in the methods, and this step can occur after assembly. The 3' and/or 5' universal flanking sequences can be the same sequence or different sequences at the 3' and 5' ends of the nucleic acid molecule of desired sequence, and can utilize sequences as described for the 3' and/or 5' primer binding sequences described herein.

While various methods of assembling DNA are available in the art, the present methods offer the ability to assemble a DNA molecule of desired nucleotide sequence where the nucleic acid molecule assembled does not comprise an expressed sequence tag; in other embodiments the oligonucleotide pairs or couplets being assembled do not comprise an expressed sequence tag; in other embodiments the method of assembly does not involve circularizing DNA or utilizing circularized DNA.

In some embodiments the universal 3' and 5' flanking sequences are removed after assembly of the nucleic acid of desired sequence, which can be done as described herein. But the universal flanking sequences can remain on the nucleic acid molecule and be used for subsequent amplification or other techniques, for example GIBSON ASSEMBLY®, or other subsequent DNA manipulation techniques.

First Amplification Reaction

The method can involve performing one or more steps of amplification of the plurality of couplets or pairs of oligonucleotides. The one or more amplification steps 101 can be performed according to any appropriate PCR method or other amplification procedure using methods and reaction parameters known to persons of ordinary skill in the art. "PCR," the polymerase chain reaction, as used herein can include variants of PCR and non-limiting examples include multiplex PCR, "hot start" PCR, polymerase cycling assembly, assembly PCR, and quantitative PCR. The Examples provide exemplary PCR amplifications, but the person of ordinary skill understands the specific reaction parameters can be varied depending on the particular oligonucleotides being assembled. Additional examples of PCR amplification methods are described in US 2014/0308710, which is hereby incorporated by reference in its entirety. Subsequent amplification step(s) can be performed until a sufficient quantity of couplets or oligo pairs has been generated.

In the first and subsequent amplification step(s) of the methods the couplets or oligonucleotide pairs can be amplified and extended. At this stage the couplets can have the 3' and 5' flanking primer binding sequences because they have been formed into a double-stranded DNA fragment 116. The primer binding sequences prevent the couplets or oligo pairs from assembling with adjacent couplets or oligo pairs in the mixture prematurely and before intended, and before sufficient amplification of the couplets or oligo pairs has occurred.

Removal of 3' and/or 5' Primer Binding Sequences/Scarless Flank Removal

The methods can also involve a step of removing the 3' and/or 5' primer binding sequences from the couplets or pairs of oligos to produce a plurality of couplets or oligonucleotides having an internal sequence, and end oligonucleotides that have the universal flanking sequences. This step can occur after one or more steps of amplification of the couplets or oligo pairs.

Previously available methods of removing primer binding sites from DNA involved the use of restriction enzymes, which leave nucleotide artifacts and unwanted nucleotide sequences. In some embodiments scarless flank removal can be performed, which allows for the removal of conserved DNA flanking sequences from PCR products and can be done without the use of any restriction enzymes. This therefore allows an unlimited number of primer binding or flanking sequences to be used because it does not rely on sequence constraints imposed by the need for restriction enzymes. The method also allows for a more robust assembly because the DNA overlaps are exposed after this removal is achieved allowing for the couplets or oligo pairs to be assembled into the desired nucleic acid sequence. An assembled product can be produced that has no extraneous, nonspecific, nucleotide remnants from restriction enzyme cleavage, or otherwise unwanted base pairs are left in the nucleic acid molecule being assembled.

Scarless flank removal exposes the overlaps between the couplet pairs and permits their assembly, and can be achieved using a number of enzymes. In some embodiments the 3' and/or 5' primer binding sequences 110, 115 present on the oligonucleotide pairs can comprise non-standard (for DNA) bases, for example deoxyuridine bases (dU) or poly dU bases, so as to be a substrate for an enzyme that selectively cleaves at the non-standard base (or base that is otherwise site specific with respect to enzyme cleavage). In some embodiments the non-standard base is dU and the enzyme is uracil-DNA glycosylase (UDG). Non-standard bases can allow the sequences to be recognized by enzymes that can remove them at an appropriate step in the methods. Thus, in some embodiments the 3' and/or 5' primer binding sequences can comprise a substrate or a sequence recognized by an enzyme (or enzymes) that specifically cleave(s) the primer binding sequences, which are thus removed. In some embodiments the specific cleavage occurs at a non-standard base (e.g. dU), but can also be sequence specific, or another means of selective cleavage, e.g. restriction cleavage. In some embodiments the 3' and/or 5' primer binding sequences comprise deoxy-uracil residues, which are substrates for UDG. In some embodiments a mixture of enzymes can be used to remove the 5' and/or 3' primer binding sequences. In some embodiments the enzyme mixture can comprise Uracil-DNA glycosylase (UDG), endonuclease VIII (Endo VIII, a DNA glycosylase-lyase), and exonuclease T (Exo T). Without wanting to be bound by any particular theory it is believed that in these embodiments the UDG catalyzes the release of uracil from uracil-containing nucleotides, leaving an apyrimidinic site and a substrate for endonuclease VIII (endo VIII). The endo VIII then acts as an AP-lyase at the resulting site. Endo VIII cleaves 3' and 5' to the AP site leaving a 5' phosphate and a 3' phosphate. Exonuclease T (a.k.a. ExoT or RNase T) is a single-stranded RNA or DNA specific nuclease that requires a free 3' terminus and removes nucleotides in the 3' to 5' direction to generate blunt ends. ExoT thus removes any single-stranded hangs remaining to yield a blunt cut DNA molecule. While this combination of enzymes represents one embodiment of a mixture of enzymes that can be conveniently used, the person of ordinary skill with reference to this disclosure will realize other combinations of enzymes that will yield a suitable result by substituting any or all of these enzymes since other enzymes can have the same or very similar activities. While these embodiments illustrate the use of dU and UDG, any non-standard nucleotide can be used that has a corresponding enzyme that will cleave the site or mark it for cleavage by another enzyme.

Assembly

For assembly of the desired DNA molecule, primers can be added to the reaction that are complementary to and bind the 3' and/or 5' primer binding sequences. In some embodiments primers used in the invention comprise a forward primer and a reverse primer. In various embodiments the methods can amplify and/or assemble at least 3 or at least 5 at least 10 or at least 50 or 3-10 or 3-20 or 3-24 or 3-30 or 3-50 or 3-60 or 3-70 or 3-80 or 3-100 or 3-120 or 5-10 or 5-30 or 5-200 or 8-15 or 10-30 or 10-50 or 25-70 or 25-100 or 25-120 or 25-150 or 25-200 or 25-225 or 25-250 or 25-300 oligonucleotide pairs or couplets (and consequently twice such numbers of oligonucleotides). In the methods the oligonucleotides form couplets as described herein.

After removal of the 3' and/or 5' primer binding sequences the resulting oligo pairs (or couplets) have overlapping, complementary regions with the adjacent pair(s) of oligonucleotides or couplet(s) and the set can be assembled into the nucleic acid molecule of desired sequence. At this step the end oligo pairs or couplets can still have the universal 3' and/or 5' flanking sequences. The nucleic acid molecule of desired sequence can also, optionally, be amplified one or more times by utilizing primers that bind to the universal 3' and/or 5' flanking sequences, 120, 125.

Any suitable method can be used to assemble the nucleic acid molecule of desired sequence, but in some embodiments polymerase cycling assembly (PCA or "assembly PCR") is used for assembly. In PCA a DNA molecule is assembled from shorter oligonucleotides in a precise order based on the single-stranded oligonucleotides used in the process. Any number of cycles of PCA or other DNA assembly procedure can be conducted to assemble the nucleic acid molecule, for example at least 5 cycles or at least 10 cycles or at least 15 cycles or at least 20 cycles or at least 25 cycles or at least 30 cycles or at least 35 cycles or at least 50 cycles. Other assembly methods, or cloning or DNA joining methods can also be used. GIBSON ASSEMBLY® is another such method that can be used to assemble the resulting DNA fragments, and embodiments are described in U.S. Pat. No. 8,968,999, which is incorporated by reference herein in its entirety, including all tables, figures, and claims. The nucleic acid molecule of desired sequence is thus assembled. This nucleic acid molecule will still contain the 3' and 5' universal flanking sequences that were present on the 3' and 5' end oligonucleotides, which can also be removed if desired. An optional, second and subsequent amplification step(s) can be performed to amplify the nucleic acid of desired sequence after this step using primers that bind to the universal flanking sequences.

The length of the oligonucleotides that form the couplets will depend on the number of couplets being assembled and the length of the nucleic acid molecule of desired sequence being assembled. In various embodiments the oligonucleotides forming the couplets can be 10-15 or 10-20 or 10-30 or 10-40 or 15-40 or 15-60 or 15-100 or 15-150 or 15-200 or 15-250 or 20-40 or 20-60 or 20-80 or 20-100 or 20-120 or 20-150 or 20-180 or 20-200 or 20-250 nucleotides in length. In other embodiments the oligonucleotides that form the couplets can be 30-40 or 30-60 or 30-80 or 30-100 or 30-120 or 30-150 or 30-180 or 30-200 or 30-250 nucleotides in length. In some embodiments the oligonucleotide pairs form a couplet through an overlapping region of at least 10 or at least 12 or at least 15 or at least 20 or at least 25 or at least 30 base pairs, which can be bound by standard Watson-Crick base pairing. In various embodiments the overlap can be expressed as a percentage of the sequence of either of the oligonucleotides, and in various embodiments at least 20% or at least 25% or at least 30% or at least 32% or at least 36% or at least 40% or at least 45% or at least 50% or 10-50% or 10-60% or 10-65% or 20-50% or 20-60% or 20-65% or 25-40% or 25-50% or 25-60% or 25-65% or 30-40% or 30-50% or 30-60% or 30-65% or less than 75% or less than 65% or less than 55% or less than 50% of the nucleotides in either of the oligonucleotides can be in the overlapping sequence to form a couplet. In various embodiments the percentages can relate to either the shorter or the longer of the two oligonucleotides. In other embodiments the oligonucleotides of the pair of are of equal length, or within 10% or 20% or 30% or 40% or 50% length of each other, and the same percentage overlap values can be used.

The nucleic acid molecule of desired nucleotide sequence to be assembled in the methods can be of any length. In some examples the nucleic acid molecule can be from about 40-100 bp or 50-100 bp or 50-150 bp or 80-120 bp or 100-1000 bp or 100-800 bp or 100-700 bp or 50-600 bp or 100-600 bp or 50-100 bp, or 50-1000 bp or 50-1500 bp, or 50-2000 bp, or 50 bp-5 kbp or 50 bp-6 kbp or 50 bp-7 kbp or 50 bp-10 kbp, or from about 1-10 kbp or from about 2-10 kbp, or from about 4-10 kbp or from about 5-10 kbp, or from about 5-15 kbp. In other embodiments the nucleic acid molecule to be assembled can have at least 100 bp and less than 1000 bp or less than 5,000 bp or less than 10,000 bp or less than 15,000 bp or less than 20,000 bp. In more embodiments the molecule can be greater than 1 kbp or greater than 2 kbp or greater than 3 kbp, or 1 kbp to about 5 kbp, or from 1 kbp to about 7 kbp, or from 1-10 kbp or from 1 kbp-12 kbp or from 1 kbp-15 kbp or from 1 kbp-16 kbp or from 1 kbp-17 kbp or from 1 kbp-20 kbp or 1 kbp-50 kbp or 1 kbp-100 kbp or 1 kbp-500 kbp or from 200-700 kbp or from 1 kb-1 Mbp, or up to 3 Mbp or up to 5 Mbp or from 1 kbp-5 Mbp, or from 1 kbp-7 Mbp, or from 1 kbp-10 Mbp.

The Method

The methods of the invention can be practiced in various embodiments depending on the specific nucleic acid molecule to be assembled. In some embodiments a method is practiced by contacting a DNA polymerase and dNTPs with a plurality of oligo pairs or couplets of the invention, such as any described herein. In the methods any number of oligonucleotide pairs or couplets described herein can be amplified and/or assembled. For example, the method can amplify and/or assemble from 2-10 oligonucleotide pairs or couplets, or from 3-10 or 3-20 or 3-30 or 3-40 or 3-50 or 3-60 or 3-70 or 3-80 or 3-100 or 3-150 or 3-200 or 3-225 oligonucleotide pairs. The length of the oligonucleotides that form the pairs that are amplified and/or assembled can be any length of oligo pairs as described herein.

The methods can involve a step of forming couplets from the various pairs of oligonucleotides that will be assembled into the DNA molecule having the desired sequence. Persons or ordinary skill with reference to this disclosure understand the temperatures the oligo pairs can be annealed into couplets, and that the specific parameters depend on the length and composition of the oligo pairs. In some embodiments the oligo pairs can be annealed at less than 55° C. or less than 50° C. or less than 45° C. or 40-55° C. or 38-55° C., or other temperatures depending on the specific oligo pairs being annealed into couplets. In various embodiments the contacting of the pairs of oligonucleotides with the DNA polymerase and dNTPs can be done in a solution or a mixture and can occur simultaneously in a single container, or can be done sequentially. The DNA polymerase can be any suitable for the circumstances, but in some embodiments will be a thermostable DNA polymerase. Examples include, but are not limited to, Taq DNA polymerase or a Pyrococcus-type DNA polymerase. As a thermostable DNA polymerase it is active at temperatures of greater than 70° C. or greater than 90° C. or greater than 98° C. In particular embodiments a Pyroccocus-like enzyme containing a processivity enhanced domain to permit increased processivity is also suitable. While any DNA polymerase may be used, a DNA polymerase delivering high accuracy and high processivity will be most effective. DNA polymerases known in the art as being high fidelity, thermophilic DNA polymerases can also be used. In some embodiments the DNA polymerase can also have 5'→3' DNA polymerase activity and/or a 3'→5' exonuclease activity. In one embodiment the DNA polymerase generates blunt ends in the amplification of products in DNA amplification reactions. Additional, non-limiting examples of DNA polymerases that can be used in the invention include DNA polymerase from *Pyrococcus furiosus*, which can be modified at one or more domains to provide greater activity and/or greater accuracy than the native enzyme. The modification can include a change in the nucleic acid sequence of the enzyme to provide for an enzyme with more advantageous properties in a DNA assembly procedure. The DNA polymerase can have all or only some of these properties, and the person of ordinary skill with resort to the present specification will realize which properties can be advantageously employed in a particular application of the methods and which reaction conditions and buffer components are appropriate for a particular DNA polymerase. Examples of DNA polymerases suitable for the present methods include the commercially available PHUSION® High Fidelity DNA polymerase (Finnzymes, Oy, FI) or VENT® DNA polymerase, which has a 3' to 5' proofreading exonuclease activity. In one embodiment a master mix can contain the DNA polymerase with MgCl$_2$ at suitable concentration (e.g., 1-2 mM or 1.5 mM), as well as a mixture of dNTPs at a suitable concentration (e.g., 200 uM of each dNTP at final reaction concentration) in 100% DMSO. But other DNA polymerases are suitable and may also be used and VENT® DNA polymerase is another example.

When uridine is utilized in the 3' and/or 5' primer binding sequences or universal flanking sequences the DNA polymerase can be a uracil-literate DNA polymerase. Uracil-literal DNA polymerases can recognize uracil in DNA templates and do not cease activity upon encountering uracil-containing nucleotides. DNA polymerases from *Pyrococcus furiosus* or from *Methanosarcina acetivorans*, or those from the Family B DNA polymerases are uracil-literate, and the person of ordinary skill will realize other DNA polymerases that are uracil-literate and that can be utilized in the invention. The DNA polymerase can also be a DNA polymerase from a single-celled organism from the taxonomic domain and kingdom of Archaea. The enzymes can be thermostable and can be designed to be faster and more accurate and/or can extend DNA synthesis further than conventional DNA polymerases. In one embodiment the DNA polymerase can read through uracil, can extend a kilobase of sequence in less than 15 seconds or less than 17 seconds, and can have an accuracy at least 20× or at least 22× or at least 24× higher than Taq DNA polymerase. VERASEQ® Ultra DNA polymerase is an example of a uracil-literal DNA polymerase that functions in the invention.

The PCR and PCA assembly procedures used in the method can be those known to persons of ordinary skill in the art and utilized according to the present disclosure. By way of example, multiple cycles of PCR or PCA (or other assembly and/or amplification reactions) can be performed for the amplification and/or assembly reactions, for example, at least 10 cycles or at least 15 cycles or at least 20 cycles or at least 25 cycles or at least 30 cycles. Each cycle can comprise an annealing phase, an extension phase, and a denaturation phase, which are defined by the physical activities performed by the DNA during each phase. In certain embodiments the annealing phase and extension phase can be combined to occur during a combined annealing and extension phase. In some embodiments the annealing phase performed at between 45° C. and 77° C., the extension phase performed at between 50° C. and 77° C., and a denaturation phase performed at greater than 70° C. or greater than 90° C. When the annealing phase and extension phase are combined into a single phase the combined phase can occur between 45° C. and 77° C., or 57-77° C., or at about 67° C. Persons of ordinary skill with resort to this disclosure will realize that the actual temperatures used during each of the phases is influenced by the size and content of the DNA being assembled. In some embodiments polyethylene glycol or another crowding agent can also be included in the mixture at an appropriate concentration, e.g. at least 0.0188% or at least 0.025% or at least 0.375%. Another crowding agent can also be used instead of or in combination with PEG, e.g., Ficoll 70, or high-mass, branched polysaccharides (e.g., dextran). When PCA is used for assembly it can utilize the same cycles and temperature ranges.

The method allows multiple nucleic acid constructs to be assembled from a single sample pool. Considering an embodiment where, for example, five oligonucleotide pairs (e.g. derived from a solid phase synthesis) are to be amplified and assembled into a DNA molecule of desired sequence, the method allows all five oligonucleotide pairs to be assembled from a single pool of oligonucleotides. Each of the five oligonucleotide pairs can be synthesized to contain a different set of 3' and/or 5' primer binding sequences. Thus, the oligo pairs (or "couplets") would have primer binding sequences as follows: couplet 1) A-B; couplet 2) C-D; couplet 3) E-F; couplet 4) G-H, couplet 5) I-J. After synthesis the oligo pairs can be combined and then divided into five pools. If one places the primers for set A-B in the first pool, and the primers for set C-D in the second pool, etc., then each couplet or oligo pair, and only that couplet or pair, will be amplified in the respective pool. In other embodiments all of the even and odd oligo pairs in a pool can have a different set of 3' and/or 5' primer binding sequences, with "even" and "odd" referring to the number assigned the oligo pair in a scheme for assembling the DNA molecule of desired sequence, for example as depicted in FIG. 3. But in other embodiments three or four or 3-8 or 3-10 or 5-10 or 5-15 or 5-20 or 5-25 or 5-30 or 5-50 or 3-200 or 3-225 or 3-250 or 3-300 couplets or oligo pairs, or any number of couplets as described herein, can be amplified and assembled, and in some embodiments from the same pool of synthesized (or parsed) oligonucleotides.

The nucleic acid molecules of desired sequence assembled by the methods can be any nucleic acid molecule or nucleic acid construct. Examples include, but are not limited to, plasmids, genes or gene families, regulatory sequences, artificial chromosomes, vector sequences, a functional gene, a CRISPR/Cas9 gRNA template, or a genome of a virus, bacteria, or algae. The construct can also be a DNA-based information storage molecule, where information is stored in the form of the number and order of nitrogenous bases with each set of bases indicating a meaningful character or value that can be deciphered into an understandable language. In some embodiments the nucleic acid molecule produced by the methods does not contain any regulatory, non-coding, or extraneous sequences that are not a part of the natural gene, i.e. the nucleic acid molecule is produced without nucleotide artifacts from the assembly and preparation procedure. Any of the nucleic acids assembled by the methods can also have one or more non-standard bases, such as 3-nitropyrrole, 5-nitroindole, deoxyuridine, and others, that have a corresponding enzyme that will cleave the site or mark it for cleavage by another enzyme.

In some embodiments the methods can be performed in one step, meaning that the oligonucleotide pairs are formed and assembled in a single container without having to open the container once the components for the assembly are added. In another embodiment the method is an automated method, meaning that no human actions are required after the components of the assembly method are placed into the container and the assembly reaction is initiated—instead the reaction goes to completion by automated methods and without further human action.

Error Suppression

Figure 6:
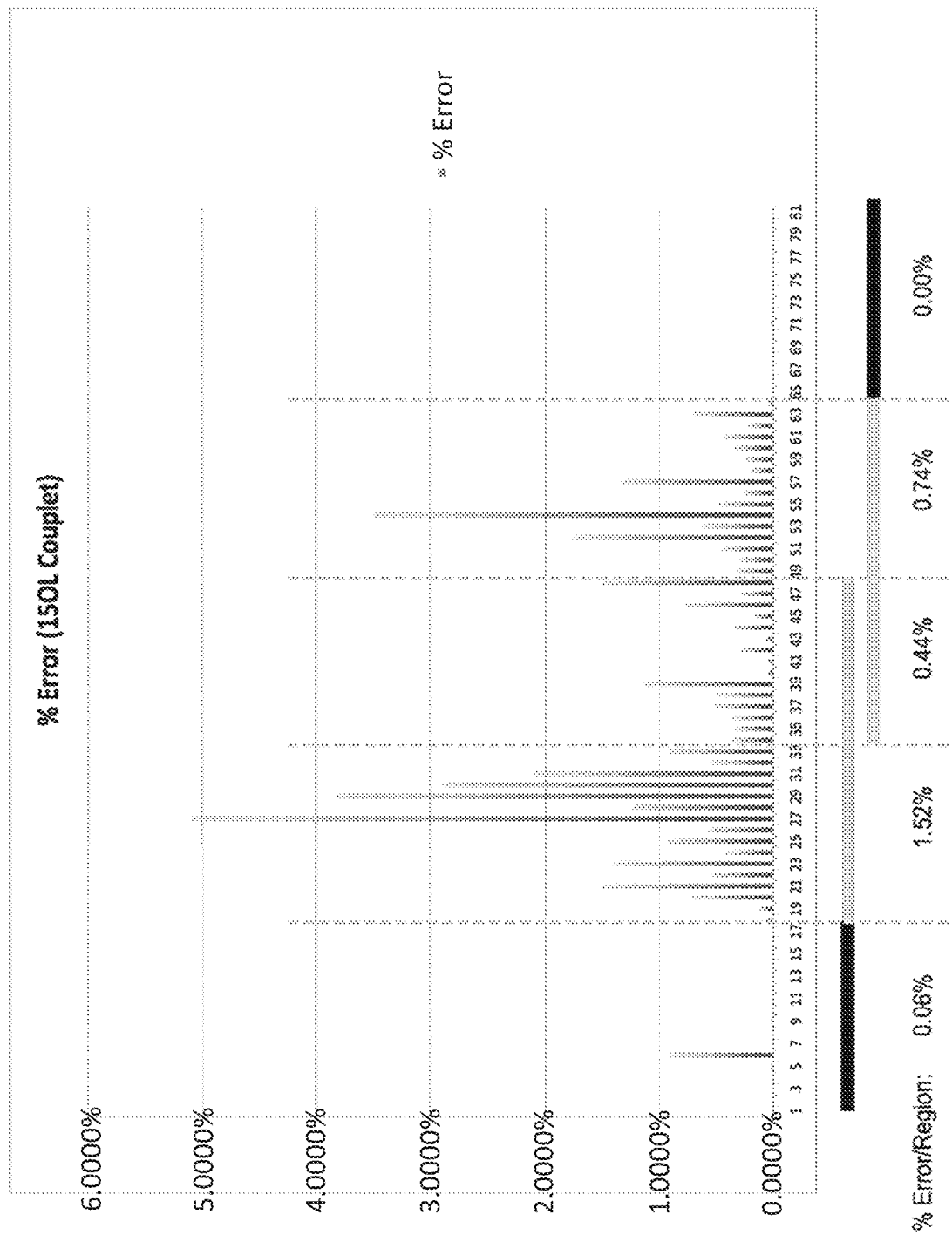
FIG. 6 provides a graphical illustration demonstrating error suppression achieved from the use of the present methods. The Figure demonstrates error rates 40%-72% lower in the overlapping regions of oligonucleotide pairs versus non-overlapping regions. An overall error frequency of 0.51% was achieved, illustrating that the methods result in nucleotide error correction.

Another benefit provided by the present invention is the ability to suppress sequencing errors. Because the method involves the annealing of oligonucleotide pairs into couplets, a natural selection against errors or sequence mismatches occurs because error-free oligos are more likely to anneal to each other and form a couplet than oligonucleotides that contain one or more errors or sequence mismatches. Error rates in the overlap sequence are at least 35% or at least 39% or at least 40% lower than in non-overlap areas of a couplet. And error rates in overlap areas are 65% or less or 61% or less or 60% or less versus non-overlap areas of a couplet. Thus, the methods are also methods for reducing or minimizing errors in an assembled nucleic acid molecule versus error rates with assembly methods that do not involve a step of couplet formation. In various embodiments the nucleic acids produced by the present methods have an error rate of less than 1.5% or less than 1.3% or less than 1.2% or less than 1.1% or less than 1.0% or less than 0.9% or less than 0.8% or less than 0.7% or less than 0.6% or less than 0.55% or less than 0.50% or less than 0.45% or less than 0.3% or less than 0.2% or less than 0.1%. Therefore, and as illustrated in FIG. 6, the methods are able to suppress errors made during at the synthesis stage of the oligonucleotides. Therefore, the invention also provides methods of synthesizing nucleic acid molecules of a desired sequence disclosed herein having an error rate disclosed herein.

Compositions

The invention also provides compositions useful for conducting the methods of the invention. In one aspect the invention provides a composition comprising a plurality of oligonucleotides formed into couplets. Each couplet can comprise a portion of a desired nucleic acid sequence, and the couplets comprise an internal sequence that comprises a portion of the desired nucleic acid sequence. When the plurality of couplets is arranged in schematic or illustrative order, adjacent to each other and according to their internal sequences they comprise at least a portion of a desired nucleic acid sequence. In some embodiments each couplet also has a 3' or a 5' primer binding sequence, and each couplet can contain a sequence that overlaps and is complementary to a portion of a sequence from at least one adjacent couplet. The desired nucleic acid sequence has a 3' end and a 5' end, and in some embodiments the couplets that make up the 3' and 5' ends of the desired sequence can also have a universal 3' flanking sequence and a universal 5' flanking sequence, respectively. The couplets in the composition can be any couplets described herein. In some embodiments the composition also contains a DNA polymerase and/or dNTPs. In some embodiments the composition is contained in a single container. The composition can further include an effective amount of a preservative. Any suitable preservative can be used such as, for example, glycerol. When glycerol is chosen as the preservative it can be present at a concentration of at least 20% or at least 30% or at least 40% or at least 50% w/w. The composition can also be present in a suitable buffer or in water. In some embodiments the couplets comprise at least 50% of the oligonucleotides in the mixture, and one or both of the oligonucleotides that form the couplets overlap at least 33% of their sequence to form the couplet.

Example 1—Assembly of 500 bp Constructs

This example illustrates the method in the partitioning and assembly of 24 DNA constructs of about 500 bp each from an oligo pool. The starting oligonucleotides were synthesized on a microarray and harvested into the oligo pool. About 10 of the oligos, when arranged adjacent to each other and in order comprise one of the 500 bp DNA constructs to be assembled. The oligos were each about 78 bp in length having a 30 bp overlap with the adjacent oligonucleotide and contained 18 bp of poly-A 3' and/or 5' flanking primer binding sites. The harvested oligo pool was diluted to a 0.25-0.5 nM average for each oligo. 24 pairs of primers containing dU and a thermostable DNA polymerase that was uracil-literate was added to the mixture.

The mixture was subjected to a PCR procedure according to the protocol shown below with partitioning primers containing dUs and using VERASEQ® DNA polymers (VSU). The product was then diluted 2× and the flanking sequences removed by scarless flank removal, with a mixture of UDG, endonuclease VIII, and exonuclease T, with an incubation for 15 min at 37° C. and 1 h at 25° C. This was then followed by 12 cycles of PCA, according to the protocol shown below. A second amplification reaction (PCR2/PCA2) was then performed for 30 cycles, as shown below using 2× PHUSION® master mix.

The result is shown in FIGS. 2a and 2b showing the result of the assembly reaction for 24 constructs at two different concentrations. 23 out of 24 of the 500 bp constructs were successfully assembled as evidenced by the bands in the expected location for 500 bp constructs.

PCR1 Program at 43-50° C.
1. 98° C. 1 min
2. 98° C. 30 sec
3. 43° C. 30 sec
4. 45° C. 30 sec, add 15 sec/cycle
5. Go to 2, 5×
6. 98° C. 30 sec
7. 45° C. 30 sec, add 15 sec/cycle
8. 47° C. 30 sec
9. Go to 6, 5×
10. 98° C. 30 sec
11. 50° C. 1 min, add 15 sec/cycle
12. Go to 10, 8×
13. 72° C. 5 min
14. 10° C. 0 (forever)

PCA Program (12 Cycles)
1. 98° C. 1 min
2. 98° C. 30 sec
3. 43° C. 30 sec
4. 45° C. 30 sec, add 15 sec/cycle
5. Go to 2, 5×
6. 98° C. 30 sec
7. 45° C. 30 sec, add 15 sec/cycle
8. 47° C. 30 sec
9. 52° C. 30 sec 10. Go to 6, 5×
11. 72° C. 5 min
12. 10° C. 0 (forever)
PCR2 Program 45-55° C. (30 Cycles)
1. 98° C. 1 min
2. 98° C. 30 sec
3. 50° C. 30 sec
4. 45° C. 30 sec, add 15 sec/cycle
5. Go to 2, 9×
6. 98° C. 30 sec
7. 48° C. 30 sec
8. 52° C. 30 sec, add 15 sec/cycle
9. Go to 6, 9×
10. 98° C. 30 sec
11. 55° C. 1 min and 30 sec, add 15 sec/cycle
12. Go to 10, 9×
13. 72° C. 5 min
14. 10° C. 0 (forever)

Example 2—Assembly of a 1.2 kb Construct

This example shows the assembly of a 1.2 kb DNA construct from oligo pools with 16, 32, and 58 oligonucleotides according to the invention. The Example also shows the robustness of the method of the invention.

Fifty-eight oligonucleotides were designed to comprise the DNA molecule of desired sequence to be assembled. The oligonucleotides were each approximately 78 bp in length and had about a 30 bp overlap with the adjacent oligo, plus an 18 bp flanking sequence on the 3' or 5' end.

The oligos were divided into three pools as follows:
a. Pool 1: The oligos were placed into four sub-pools with 16, 16, 16, and 10 oligos resulting in a concentration of 5 nM for each oligo.
b. Pool 2: The oligos were placed into two sub-pools with 32 and 26 oligos resulting in a concentration of 2.5 nM for each oligo.
c. Pool 3: All 58 oligos were provided as one pool at 1.25 nM concentration for each oligo.

A PCR procedure was set up using the protocol in Example 1 and using primers containing dUs and using VERASEQ® Ultra DNA polymerase (VSU). The couplets for each of the pools were subjected to scarless flank removal, as described above and the 3' or 5' flanks removed using a mixture of UDG, Endo VIII, and exonuclease T per 10 ul of reaction. Twelve cycles of PCA was performed, again as described in Example 1. PCR was performed on the assembled construct using 2× PHUSION® master mix and the same PCR protocol in Example 1. PCR was performed again with 2 ul of the PCA reaction as described above.

| Pool # | # of sub-pools | # of oligos in a sub-pool | Oligo conc. (nM) | # of cPCR | pool cPCR as one | SFR Treatment | PCA assembly | 1.2 kb formed |
|---|---|---|---|---|---|---|---|---|
| 1 | 4 | 16, 16, 16, 10 | 5 | 4 | yes | yes | yes | yes |
| 2 | 2 | 32, 26 | 2.5 | 2 | yes | yes | yes | yes |
| 3 | 1 | 58 | 1.25 | 1 | na | yes | yes | yes |

As illustrated in Table 1 above, the method assembled the 1.2 kb construct from oligo pools in all three groups, demonstrating the robustness of the method. FIG. 7 provides a gel demonstrating the assembly of the 1.2 kb product.

Although the disclosure has been described with reference to the above examples, it will be understood that modifications and variations are encompassed within the spirit and scope of the disclosure. Accordingly, the disclosure is limited only by the following claims.

The invention claimed is:

1. A method of assembling a double-stranded DNA molecule (dsDNA) having a desired sequence comprising:
    a) contacting a DNA polymerase, dNTPs, and a plurality of pairs of oligonucleotides, wherein each oligonucleotide of a pair comprises a portion of the desired sequence, and the oligonucleotides of a pair comprise an internal sequence that overlaps and is complementary to an internal sequence of the other oligonucleotide of the pair;
    wherein when the plurality of pairs of oligonucleotides are arranged in order, adjacent to each other and according to their internal sequences they comprise at least a portion of the desired sequence;
    wherein the oligonucleotides comprise a 3' or a 5' primer binding sequence that comprises at least one non-standard base;
    wherein the dsDNA molecule of desired sequence has a 3' end and a 5' end, and the oligonucleotide pairs that comprise the 3' and 5' ends further comprise a universal 3' flanking sequence and a universal 5' flanking sequence comprised to the inside of the 3' and 5' primer binding sequences, respectively, and wherein the oligonucleotide pairs that do not comprise the 3' and 5' ends of the dsDNA molecule of the desired sequence, do not comprise a universal 3' flanking sequence or a universal 5' flanking sequence;
    b) performing a first amplification reaction on the plurality of pairs of oligonucleotides using primers that bind to the 3' and 5' primer binding sequence;
    c) removing the 3' and 5' primer binding sequences from the plurality of pairs of oligonucleotides using an enzyme that specifically cleaves the primer binding sequences at a non-standard base; and
    d) subjecting the plurality of pairs of oligonucleotides to an assembly reaction to thereby assemble the dsDNA molecule having the desired sequence.

2. The method of claim 1 further comprising a step of removing at least a portion of the universal 3' flanking sequence and the universal 5' flanking sequence.

3. The method of claim 1 wherein the first amplification reaction comprises a denaturation phase, an annealing phase, and an extension phase.

4. The method of claim 3 wherein the amplification reaction is the polymerase chain reaction, or a variant of PCR.

5. The method of claim 1 further comprising a second, and optionally additional, amplification reactions.

6. The method of claim 1 wherein the 5' and 3' primer binding sequences on an oligonucleotide pair are not complementary to each other.

7. The method of claim 1 wherein the method assembles a plurality of DNA molecules of desired sequences.

8. The method of claim 7 wherein the plurality of DNA molecules comprises a plurality of distinct genes.

9. The method of claim 1 wherein the pairs of oligonucleotides are comprised on a solid support.

10. The method of claim 9 wherein the solid support is a nucleic acid array.

11. The method of claim 10 wherein at least 15 pairs of oligonucleotides are comprised on the array.

12. The method of claim 1 wherein the oligonucleotides comprise from 60 to 100 nucleotides and the primer binding sequences comprise from 8 to 30 nucleotides.

13. The method of claim 12 wherein the dsDNA molecule assembled is a nucleic acid construct selected from the group consisting of: a plasmid, an artificial chromosome, and a functional gene.

14. The method of claim 4 wherein a first pair of oligonucleotides comprises a first set of 3' or 5' primer binding sequences, and a second pair of oligonucleotides comprises a second set of 3' or 5' primer binding sequences.

15. The method of claim 1 wherein the 3' and 5' primer binding sequences do not comprise a restriction site for a restriction enzyme.

16. The method of claim 1 wherein the 3' and 5' primer binding sequences are removed by the action of one or more enzymes that specifically cleave the primer binding sequences, and wherein the one or more enzymes do not comprise a restriction enzyme.

17. The method of claim 16 wherein the one or more enzymes comprise uracil DNA glycosylase, endonuclease VIII, and exonuclease T.

18. The method of claim 1 further comprising a step of pre-determining the sequence of the desired DNA molecule.

19. The method of claim 1 wherein a plurality of oligonucleotide pairs is comprised in a single container and forms at least two couplets, and the at least two couplets comprise distinct sets of 3' and 5' primer binding sequences, and the primers comprise two sets of primers that bind specifically to the at least two couplets.

20. The method of claim 1 further comprising a step of forming the plurality of pairs of oligonucleotides into a plurality of couplets.

21. The method of claim 1 performed in a single container.

22. The method of claim 1 which is an automated method.

23. The method of claim 1 wherein the oligonucleotides comprised in the pairs of oligonucleotides are from about 50 to about 200 nucleotides in length.

24. The method of claim 1 wherein the dsDNA molecule assembled in the method is greater than 5 Mbp in size.

25. The method of claim 1 wherein the nucleic acid molecule of desired sequence is a scarless DNA molecule.

26. The method of claim 1 wherein step (d) comprises the use of primers that bind to the universal 3' and 5' flanking sequences.

* * * * *